United States Patent
Shear et al.

(10) Patent No.: US 9,173,941 B1
(45) Date of Patent: Nov. 3, 2015

(54) SUSTAINED RELEASE BITTERING COMPOSITION

(71) Applicants: Jeff Shear, Glenview, IL (US); Alvin Kershman, Chesterfield, MO (US)

(72) Inventors: Jeff Shear, Glenview, IL (US); Alvin Kershman, Chesterfield, MO (US)

( * ) Notice: Subject to any disclaimer, the term of this patent is extended or adjusted under 35 U.S.C. 154(b) by 71 days.

(21) Appl. No.: 13/954,463

(22) Filed: Jul. 30, 2013

Related U.S. Application Data

(60) Provisional application No. 61/678,705, filed on Aug. 2, 2012.

(51) Int. Cl.
*A61K 47/18* (2006.01)
*A61K 47/26* (2006.01)
*A61K 31/192* (2006.01)
*A61K 31/5377* (2006.01)
*A61K 31/205* (2006.01)

(52) U.S. Cl.
CPC .............. *A61K 47/186* (2013.01); *A61K 31/192* (2013.01); *A61K 31/205* (2013.01); *A61K 31/5377* (2013.01); *A61K 47/26* (2013.01)

(58) Field of Classification Search
None
See application file for complete search history.

(56) References Cited

U.S. PATENT DOCUMENTS

| | | | |
|---|---|---|---|
| 4,937,078 A | 6/1990 | Mezei et al. | |
| 4,945,084 A | 7/1990 | Packman | |
| 5,002,974 A | 3/1991 | Geria | |
| 5,276,032 A | 1/1994 | King et al. | |
| 5,314,915 A | 5/1994 | Rencher | |
| 5,447,930 A | 9/1995 | Nayak | |
| 6,274,555 B1 | 8/2001 | Berdami | |
| 8,104,433 B2 | 1/2012 | Clement et al. | |
| 2005/0020537 A1 | 1/2005 | Leung et al. | |
| 2005/0100621 A1* | 5/2005 | Popp et al. ................... | 424/776 |
| 2006/0222684 A1* | 10/2006 | Isele ............................. | 424/442 |
| 2007/0110880 A1* | 5/2007 | Thomas et al. ............... | 426/623 |
| 2007/0298013 A1* | 12/2007 | Altman ........................ | 424/93.3 |
| 2008/0075793 A1 | 3/2008 | Dunshee et al. | |
| 2008/0085245 A1* | 4/2008 | Sheil et al. ................... | 424/10.1 |
| 2008/0131527 A1 | 6/2008 | Sheil et al. | |
| 2010/0016462 A1* | 1/2010 | Clement et al. ............... | 523/105 |
| 2010/0233292 A1 | 9/2010 | Rocker et al. | |
| 2011/0189160 A1 | 8/2011 | Bartels | |
| 2011/0230816 A1 | 9/2011 | Copp-Howland | |
| 2012/0004303 A1 | 1/2012 | Benson et al. | |
| 2012/0128805 A1 | 5/2012 | Clement et al. | |
| 2012/0148520 A1 | 6/2012 | Strobel et al. | |
| 2012/0164228 A1 | 6/2012 | Suplie | |

* cited by examiner

*Primary Examiner* — Theodore R West
(74) *Attorney, Agent, or Firm* — CreatiVenture Law; Linda L. Lewis

(57) ABSTRACT

A sustained release lotion for deterring animals from licking made by combining an aqueous phase having at least one bittering agent and at least one humectant, herein the at least one bittering agent is present in the aqueous phase in the range of about 0.001 to 25.0 wt. %; wherein the humectant is present in the aqueous phase in the range of from about 1 to 99 wt. %; and an oil phase comprising at least one oil and at least one surfactant, wherein the surfactant is present in the oil phase in the range of from about 1 to 100 wt. %, and wherein the aqueous phase is added to the oil phase in a weight ratio of about 3:1 to 49:1 using low to medium shear mixing and wherein the lotion is hydrophobic and has sustained release properties.

13 Claims, No Drawings

SUSTAINED RELEASE BITTERING COMPOSITION

CROSS-REFERENCE TO RELATED APPLICATIONS

This application claims the benefit of provisional patent application Ser. No. 61/678,705 filed on Aug. 2, 2012.

STATEMENT REGARDING FEDERALLY SPONSORED RESEARCH

Not Applicable.

APPENDIX

Not Applicable.

BACKGROUND OF THE INVENTION

1. Field of the Invention

This invention relates to a sustained release composition useful to deter wound licking by an animal through gustatory aversion, and the uses of such compositions for this purpose.

2. Related Art

An animal having a lesion or affliction, or a bandage or other foreign object, such as a medical device, on its body tends to lick or bite at the lesion or superficial affliction or molest or attempt to remove the bandage or foreign object. This behavior results in the lesion taking longer to heal or the bandage or foreign object being nonfunctional for its purpose. One way this problem has been addressed in the past is by the use of head cones, also known as Elizabethan collars, to prevent the animal's access to the area with its mouth. However, head cones have many disadvantages. Often the head cone must be worn for several days, putting undue leverage and pressure on the animal's neck. Further, head cones are impractical to use if the animal must be crated in order to limit activity or is too large. For a domestic animal, enduring the physical burden and visual limitations of a head cone can easily result in the animal damaging furniture and harming itself. The unnatural circumstance of having to endure a head cone and an increased sense of vulnerability due to a reduced field of vision can increase stress levels.

Another method of addressing this problem involves the application of bitter tasting substances. One such substance is a spray sold under the tradename Grannick's Bitter Apple®. Another is a topical spray with an added antiseptic agent sold under the tradename Wound-Gard® by Virbac. A gel sold under the tradename Yuk® 2e by Vet Planet can be applied directly to the animal's wound or bandage. Yuk® 2e is a combination of denatonium and sucrose octaacetate and is extremely offensive to the animal, yet harmless. In all these products, animals are dissuaded from molesting, licking, chewing or biting or self-traumatizing wounds, sutures, dressings, and the like by the bitter taste of the composition. However, none of these products provides long-lasting deterrence. Each requires relatively frequent re-application. In both veterinary and home environments, this frequent need for attention puts an undue burden on the animal's caretaker and may serve to contaminate surfaces with which the animal comes into contact.

Disclosed herein are compositions comprising a sustained release bittering agent. The compositions are useful for modifying the behavior of an animal. For example, the compositions are especially useful for deterring an animal from licking a particular area or object. It is particularly useful for deterring an animal from licking an area, such as a lesion, superficial affliction and the like in order to allow the area to remain unmolested or the lesion to heal.

SUMMARY OF THE INVENTION

The present invention relates to a sustained release composition for deterring animals from licking comprising a lotion made by combining an aqueous phase comprising at least one bittering agent and at least one humectant, wherein the at least one bittering agent is present in the aqueous phase in the range of about 0.001 to 25.0 wt. %; and wherein the at least one humectant is present in the aqueous phase in the range of from 1 to 99 wt. %. and an oil phase comprising optionally at least one surfactant, and optionally at least one oil, wherein the surfactant is present in the oil in the range of from about 1 to 100 wt. %. The aqueous phase is added to the oil phase in a weight ratio of about 3:1 to 49:1, and wherein the aqueous phase is added to the oil phase using low to medium shear mixing to provide the lotion, and wherein the lotion is hydrophobic and has sustained release properties.

In a preferred embodiment, the oil phase comprises at least one oil and at least one surfactant, wherein the surfactant has a HLB of less than 4.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION OF THE PREFERRED EMBODIMENTS

The following description of the preferred embodiment(s) is merely exemplary in nature and is in no way intended to limit the invention, its application, or uses.

The term "animal" means any animal, including livestock, such as horses, cows, goats and pigs. It also includes domesticated animals. Preferably, the animal is a domestic animal such as canine or feline. Most preferably, the animal is canine.

Bitterants are chemicals that are non-toxic, but can be added to a product to make it smell and/or taste bad. Useful bitterants are well known to those of skill in the art. In preferred embodiments, the one or more bitterant(s) present in the gustatory and/or olfactory aversion compositions disclosed herein is/are included in but not limited to the group of denatonium, sucrose octaacetate, quinine sulfate, naringen and citronella. When denatonium is present, it can be in any useful form, such as a salt. Most preferably, it is present in its salt form as denatonium benzoate. When quinine is present, it can be in any useful form, such as a salt. Most preferably, it is present in its salt form as quinine sulfate. When more than one bitterants are used, they can be pre-mixed together before adding to the composition.

In another embodiment, disclosed herein is a method of modifying an animal's behavior. The method comprises contacting an area accessible to the animal with a composition as described herein. Specifically, disclosed is a method of deterring an animal from licking, chewing, biting, or molesting in any way, an area, the method comprising, contacting the area to be protected from the molesting, licking and the like or contacting in the vicinity thereof with a composition disclosed herein, wherein the molesting, licking and the like is deterred. The method is not limited to licking, and includes chewing, biting, or any other unwanted behavior such as molesting which can be deterred by gustatory and/or olfactory aversion. The method further comprises subsequently applying additional composition to the area to be protected.

The presently claimed gustatory and/or olfactory aversion compositions advantageously provide a long-lasting effect. The composition promotes prolonged contact and interaction of the bitterants with the animal's taste receptors and all intra-oral surfaces thereby extending gustatory and olfactory experiences. Even the usual ptyalism (hypersalivation) by the animal will not effectively dilute the bitterants' intra-oral residency time and effect. The composition allows the bitterant to stick to the area or the vicinity thereof to be protected as well as to the animal's intra-oral surfaces. Intra-oral surfaces include all posterior and anterior structures associated with the mouth, including, lips, gums, teeth, palate, uvula and tongue. This feature is unlike prior art compositions, which have to be re-applied frequently. Further, this feature results in the animal safely sensing by taste, smell or mouth-feel the composition for a longer period. Thus, the animal continues to sense the bitterant longer. The extended time the bitterant is sensed results in the animal more likely remembering the strong deterrent or associating the behavior, i.e. molesting, licking, and the like with the bitterant. Thus, the long-lasting gustatory and/or olfactory aversion composition provides advantages for behavior modification.

"Sustained release properties" is defined as the properties of the lotion, i.e., the deterrent to licking, lasts at least twenty-four hours, and more preferably forty-eight hours. Most preferably the deterrent is effective from twenty-four to seventy-two hours.

The area which the animal is being deterred from molesting, licking, chewing, biting and the like can be any area amenable to contacting with a composition disclosed herein. The area does not need to be on the animal's body. The method covers any area accessible, reachable or available to the animal which can be a part or on the animal's body or can be a separate area that the animal can access or reach. Non-limiting examples of these areas include furniture and walls. However, the compositions disclosed herein are particularly useful for deterring an animal from molesting, licking and the like a lesion or affliction on its body so that the lesion or affliction can properly heal. The lesion or affliction can be any cut or wound, including burns, abrasions, surgical incisions, including sutures, dressings, allergic reaction, bites, sores, broken skin, and the like and "hot spots." The composition can be applied directly to a lesion or affliction. More preferably, the compositions are applied adjacent to the area to be protected. This includes the fur or skin at or adjacent to the outer edge of the lesion, superficial affliction, foreign object and the like and extending out as far as necessary to deter molesting, licking and the like of the area to be protected. The area in vicinity thereof also includes any bandage or dressing that can cover the area, e.g. a bandage covering at least a portion of the lesion, etc. The area can also include a device on the animal that would benefit from the animal not licking or molesting it. Examples of such devices include IV lines and indwelling catheters of any kind.

Any suitable type of anesthetic agent or combination of agents can be used. Lidocaine, chloroprocaine, mepivacaine, bupivacaine, articaine, etidocaine, levobupivacaine, tetracaine, prilocaine, benzocaine, ropivacaine, oxyprocaine, hexylcaine, dibucaine, piperocaine and procaine and pharmaceutically acceptable acids, bases and salts thereof, for instance, may be suitable anesthetic agents.

Other potential anesthetic agents include: butamben, butambenpicrate, dimethisoquin hydrochloride, diperodon, ketamine, p2-(die-ethylamino) ethyl ester hydrochloride, pramoxine and their salts, such as pramoxine HCl. A preferred anesthetic is pramoxine hydrochloride, which is present in the composition from about 0.1 to 5.0 wt. %.

Potential analgesic anti-inflammatory agents include the following: acetaminophen, aspirin, salicylic acid, methyl salicylate, choline salicylate, glycol salicylate, 1-menthol, camphor, mefenamic acid, fluphenamic acid, indomethacin, diclofenac, alclofenac, ibuprofen, ketoprofen, naproxen, pranoprofen, fenoprofen, sulindac, fenbufen, clidanac, flurbiprofen, indoprofen, protizidic acid, fentiazac, tolmetin, tiaprofenic acid, bendazac, bufexemacpiroxicam, phenylbutazone, oxyphenbutazone, clofezone, pentazocine, mepirizole, hydrocortisone, cortisone, dexamethasone, fluocinolone, triamcinolone, medrysone, prednisolone, flurandrenolide, prednisone, halcinonide, methylprednisolone, fludrocortisone, corticosterone, paramethasone, betamethasone, suprofen, piroxicam, diflunisal, and meclofenamate sodium. Preferably, the anti-inflammatory is present in the composition from about 0.1 to 5.0 wt. %.

The composition preferably includes an antiseptic agent to, amongst other things, minimize wound contamination and infection. Any suitable type of antiseptic agent can be used. Suitable antiseptic agents include cetrimide, povidone-iodine, chlorhexidine, iodine, benzalkonium chloride, nitrofurazone, benzoyl peroxide, hydrogen peroxide, resorcinol and cetylpyridinium chloride. The composition preferably includes cetrimide within a range of about 0.1 wt. % to about 5 wt. %.

The composition optionally includes an anti-bacterial agent. Suitable agents include silver sulfadiazine, triclocarban, chlorhexidine, alexidine, polymeric biguanides, triclosan, PCMX (p-chloro-m-xylenol), silver compounds, cetrimide, benzalkonium chloride, and cetylpyridinium chloride. A preferred anti-bacterial is silver sulfadiazine. The composition preferably includes the anti-bacterial agent within a range of about 0.1 wt. % to about 5 wt. %.

Optionally, the composition includes an insecticide or insect repellent to stop insects from infesting the open wound. Any suitable type of insecticide or insect repellent can be used. Examples of suitable insecticides include: trichlorfon, fenthion, cyromazine, dicyclanil, fluazuron, amitraz, flumethrin, ivermectin, doramectin, moxidectin, spinosad, imidacloprid, nitenpyran, pyriproxysen, cythioate, lufenuron, selamectin, milbemycin oxime, propetamphos.

The oil phase is prepared from a hydrophobic solution or mixture containing optionally at least one oil or petroleum distillate and at least one surfactant. The surfactant is preferably a non-water soluble surfactant having an HLB number of less than 4, and includes emulsifiers. Examples of suitable surfactants include oleic acid, acetylated monoglycerides, glycerol dioleate, sorbitan tristearate, glycerol monoleate, acetylated monoglycerides and various combinations of these. A preferred surfactant is commercially sold as ATMOS 300K, and is a combination of mono- and diglycerides made from edible food sources and propylene glycol.

The surfactant is present in the oil phase in the amount of about 1 to 100%. The optional oil suitable for the oil phase is typically liquid or semi-solid at room temperature, and is compatible with wounds, the epidermis and the oral cavity. Such oils include plant oils, such as vegetable oil, corn oil, canola oil, coconut oil, castor oil or olive oil, and animal fats such as tallow and lard. The oils include petroleum distillates, such as petrolatum and mineral oil. Mixtures of oils are also contemplated in the present invention. The oil phase is present in the composition in the range of from about 2 to 25 wt. %. In a preferred embodiment, the oil and the surfactant are present in the composition in a weight ratio of about 2:1 to 1:2.

The aqueous phase contains at least one humectant and at least one bittering agent. Suitable humectants include, but are not limited to glycerine, lactic acid, polyols, propylene glycol, corn syrup, and sorbitol. A preferred combination of humectants is glycerin and sorbitol. A preferred form of sorbitol is non-crystallizing liquid sorbitol (70 wt. % sorbitol in water). The combination of glycerin and non-crystalizing liquid sorbitol provides additional stability to the composition. The ratio of glycerin to non-crystalizing liquid sorbitol is from 1:2 to 2:1. Most preferably, the ratio is about 1:1. The at least one humectant is present in the aqueous phase from 1 to 99 wt. %. The amount of at least one humectant in the composition is from about 1 to 99 wt. %. Preferably, the amount of humectant is from about 50 to 99 wt. %. More preferably, the amount of humectant in the composition is from about 75 to 99 wt. %.

The term "sustained release" refers to the prolonged release of the bitterant from the lotion, which is only activated when licked by the animal. Because the lotion is not removed by licking or washing, the release is "sustained release." The deterrent to licking lasts at least twenty-four hours, preferably forty-eight hours, and most preferably the deterrent is effective from twenty-four to seventy-two hours.

Other additives suitable for the present invention include, but are not limited to, colorings, flavorings and abrasives.

The claimed composition is typically prepared using a planetary or counter rotating type mixer having a rubber lined mixing bowl equipped with a rubber coated wire whip stirring device. The aqueous phase is blended at relatively low shear (30-600 rpm's) into the oil phase, continuously forming a total encapsulation of the aqueous solution droplets by the oil. This process is enhanced significantly by the oil wet-able properties of the rubber lining of the mixing bowl. Rubber coating of the wire whip device improves the rate of processing.

In an embodiment of the invention, the process of preparing the composition is conducted in 2 steps:

Step 1 produces a seed batch for further processing. The initial seed batch is produced by adding a small volume of oil phase to the lined mixing chamber or bowl at a sufficient depth that the wire whip or mixing device touches the oil while rotating. The wire whip is then engaged at rate of about 30 to 100 rpm's. The aqueous phase is added at a rate approximately equivalent to the initial volume of the oil solution per minute. That is, if the initial volume of the oil phase is 20 mL, then the aqueous phase is added at a rate of about 20 mL per minute while being mixed in at 30 to 100 rpm's. Once, the desired weight ratio of aqueous phase to oil phase is reached (about 3:1 to 49:1), this initial process step is concluded.

Step 2 begins with the seed batch of Step 1, at the desired final weight ratio of aqueous phase to oil phase. The volume of seed material needed for Step 2 is to about 5-20 volume % of the final mixing chamber volume. The mixing whip or equivalent stirring and folding device are engaged at a speed of about 50 to 600 rpm's. The oil and water phases are added separately and simultaneously to the starter batch at a ratio equal to that contained in the seed batch. The rate of adding the two separate solutions is about 1 to 5% of the mixing chamber capacity per minute. As the mixing bowl or chamber fills, excess liquid may be removed continuously without halting the process. Alternatively, the process can be halted for partial or entire contents removal. Once the process is halted and a portion of the contents removed, the retained material can be held for an extended period of time. Because coating of and encapsulation of the aqueous phase is almost immediate, and materials are mixed at final required ratio in step 2, all product produced at any time during step 2 is ready to use.

In another embodiment of the invention, the lotion is prepared as is disclosed in Example 1, below.

Example 1

TABLE 1

Sustained Release Bittering Composition

| Ingredient | Wt. % | Mass for 1300 g batch |
|---|---|---|
| Citation 70 mineral oil | 4.20 | 54.60 |
| Atmos 300 ® surfactant | 2.62 | 34.06 |
| 70% sorbitol solution humectant | 45.59 (31.91% sorbitol and 13.68% water) | 592.67 |
| Glycerin humectant | 45.59 | 592.67 |
| 5% denatonium benzoate solution bittering agent | 1.00 (0.05% denatonium and 0.95% water) | 13.00 |
| Pramoxine Hydrochloride anesthetic | 1.00 | 13.00 |
| Total | 100 | 1300 |

Since the denatonium benzoate is present as a 5 wt. % solution and the sorbitol is in a 70 wt. % solution, the total water in the composition is 14.63 wt. %.

Method of Preparing the Lotion

A. Preparing Denatonium Benzoate Solution
1. To form the 5% solution, add denatonium benzoate to distilled water (approx. 26.7° C.) and stir 10 min. till dissolved.
2. Maintain minimal agitation throughout remainder of process.

B. Preparing Oil Phase (6.82 wt. % of Final Composition)
1. Warm mineral oil to 26.7° C.
2. Add Atmos® 300K, mix well and set aside.

C. Preparing the Aqueous Phase (93.18 wt. % of the Final Composition)
1. Mix the sorbitol solution and glycerin together. Add the 5% denatonium benzoate solution. Mix well and warm to 43.33° C.
2. Add the pramoxine hydrochloride and mix well at 43.33° C. until dissolved and clear.
3. Remove heat source.

D. Forming the Lotion
1. Using a 5 quart lab Hobart type planetary lab/kitchen mixer with a rubber or plastic lined wire whip and rubber or plastic lined bowl add 40 g of oil phase and stir on #2 setting.
2. Slowly add approx. 200-300 g aqueous phase with mixing.
3. Add remainder of the oil phase to the bowl. Slowly add remainder of the aqueous phase to the bowl with mixing. Scrape the sides of the bowl with a spatula to ensure thorough mixing.
4. Increase the speed to #4 for 10 minutes more, making sure to scrape the sides of the bowl occasionally. After 10 minutes, the lotion is prepared.

The lotion of Example 1, Table 1, above, is viscous, pourable, non-water dispersible and has sustained release properties.

The lotion of Example was tested on ten post-surgical canines. For eight of the ten test animals, the lotion was found to be effective in eliminating post-surgery licking of the incision. Because it is hydrophobic, the lotion could not be washed off with water, but could be removed with alcohol wipes. Likewise it was not easily licked off by the animals. The lotion remained effective for at least 24 hours.

Example 2

TABLE 2

Sustained Release Bittering Composition with Anti-inflammatory

| Ingredient | Wt. % |
|---|---|
| Citation 70 mineral oil | 7.00 |
| Atmos 300 ® surfactant | 7.00 |
| 70% sorbitol solution humectant | 41.5 (29.0% sorbitol and 12.5% water) |
| Glycerin humectant | 41.5 |
| 5% denatonium benzoate solution bittering agent | 1.00 (0.05% denatonium and 0.95% water) |
| Pramoxine Hydrochloride anesthetic | 1.00 |
| Hydrocortisone Acetate | 1.00 |
| Total | 100 |

Example 2 is prepared according to the same method disclosed for Example 1. An anti-inflammatory agent, hydrocortisone acetate, is added to the aqueous phase. Additional ingredients can be added to this formulation, such as the addition of an anti-bacterial agent. For example, 1.0 wt. % of silver sulfadiazine can be added to the lotion.

The embodiments were chosen and described to best explain the principles of the invention and its practical application to persons who are skilled in the art. As various modifications could be made to the exemplary embodiments, as described above with reference to the corresponding illustrations, without departing from the scope of the invention, it is intended that all matter contained in the foregoing description and shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

What is claimed is:

1. A sustained release composition to deter animal wound licking comprising a lotion made by the process of combining:
   A) an aqueous phase comprising an aqueous solution or suspension containing at least one bittering agent and at least one humectant, wherein the at least one bittering agent is present in the aqueous phase in the range of about 0.001 to 25.0 wt. %; and wherein the at least one humectant is present in the aqueous phase in the range of from about 0.1 to 99 wt. %, and
   B) an oil phase comprising at least one surfactant, and optionally at least one oil, wherein the at least one surfactant is present in the oil phase in the range of from about 1 to 100 wt. %; wherein the aqueous phase is added to the oil phase in a weight ratio of about 3:1 to 49:1, and the aqueous phase is added to oil phase using low to medium shear mixing to provide the lotion, wherein the lotion is hydrophobic and has sustained release properties; wherein the humectant is a combination of glycerine and sorbitol.

2. The composition of claim 1, wherein the surfactant has an HLB of less than 4.

3. The composition of claim 1, wherein the surfactant is selected from the group consisting of oleic acid, acetylated monoglycerides, glycerol dioleate, sorbitan tristearate, glycerol monoleate, acetylated monoglycerides, propylene glycol monoglyceride, propylene glycol diglyceride and combinations thereof.

4. The composition of claim 1, wherein the bittering agent is a water soluble salt of denatonium.

5. The composition of claim 1, wherein the humectant is present in the composition from about 50 wt. % to about 99 wt. %.

6. The composition of claim 1, wherein the humectant is present in the composition from about 75 wt. % to about 99 wt. %.

7. The composition of claim 1, wherein the sorbitol is non-crystallizing liquid sorbitol.

8. The composition of claim 1 wherein the lotion also contains an anesthetic.

9. The composition of claim 8, wherein the anesthetic is pramoxine hydrochloride.

10. A sustained release composition to deter animal wound licking comprising a lotion comprising:
   from about 50 to 99 wt. % humectant;
   from about 1 to 50 wt. % water;
   from about 0.001 to 5.00 wt. % bittering agent;
   from about 0 to 25 wt. % oil;
   from about 25 to 1 wt. % surfactant;
   wherein the lotion is hydrophobic and has sustained release properties;
   wherein the humectant is a combination of glycerine and sorbitol.

11. The composition of claim 10, wherein the surfactant is selected from the group consisting of oleic acid, acetylated monoglycerides, glycerol dioleate, sorbitan tristearate, glycerol monoleate, acetylated monoglycerides, propylene glycol monoglyceride, propylene glycol diglyceride and combinations thereof.

12. The composition of claim 10, wherein the humectant is present in the composition from about 50 wt % to about 99 wt %.

13. The composition of claim 10, wherein the sorbitol is non-crystallizing liquid sorbitol.

* * * * *